United States Patent
Vanmoor

[11] Patent Number: 5,845,642
[45] Date of Patent: Dec. 8, 1998

[54] SAFE SEX ASSURANCE DEVICES

[76] Inventor: Arthur Vanmoor, 153 E. Palmetto Park Rd., Suite 219, Boca Raton, Fla. 33432

[21] Appl. No.: 921,899

[22] Filed: Sep. 2, 1997

[30] Foreign Application Priority Data

Sep. 1, 1996 [NL] Netherlands .......................... 1003937

[51] Int. Cl.⁶ .................................................. A61B 19/00
[52] U.S. Cl. .......................................... 128/869; 128/883
[58] Field of Search ..................................... 128/842, 844, 128/869, 918, 883, 884; 600/38–41; 604/347–353

[56] References Cited

U.S. PATENT DOCUMENTS

| | | | |
|---|---|---|---|
| 32,842 | 7/1861 | Reynolds | 128/883 |
| 742,814 | 10/1903 | Todd | 128/883 |
| 745,264 | 11/1903 | Todd | 128/883 |
| 5,370,130 | 12/1994 | Hess | 128/844 |
| 5,370,131 | 12/1994 | Hess | 128/884 |
| 5,715,839 | 2/1998 | Strauss | 128/844 |

Primary Examiner—Michael A. Brown
Attorney, Agent, or Firm—Herbert L. Lerner; Laurence A. Greenberg

[57] ABSTRACT

A device which is worn as an undergarment which cannot be removed without destroying the device. The device is worn in order to guarantee that the wearer has been sexually faithful to ones partner. The device comprises a plurality of loop members and a plurality of longitudinal members interconnecting the plurality of loop members. The device also has a testicle retaining ring having a locking member disposed thereon and attached to one of the longitudinal members. The locking member adjusts and maintains a selected circumference of the retaining ring.

7 Claims, 3 Drawing Sheets

SAFE SEX ASSURANCE DEVICES

BACKGROUND OF THE INVENTION

1. Field of the Invention

The invention relates, generally, to safe sex assurance devices and, more specifically, it relates to an inexpensive and disposable device to be worn particularly by men and also women.

2. Description of the Related Art

In general, safe sex assurance devices such as chastity belts are well known in the art. Prior art chastity belts usually consist of an undergarment made of a durable material such as leather and a locking device. The locking device is opened by a key for removal of the undergarment.

In view of the advent of the AIDS crisis and other sexually transmitted diseases, the popularity of chastity belts is increasing. Prior-art chastity belts are generally expensive, bulky and uncomfortable to wear. In addition, safe sex assurance devices have been generally marketed for use by women and there is generally a lack of such devices for men.

SUMMARY OF THE INVENTION

It is accordingly an object of the invention to provide safe sex assurance devices, which overcome the herein-mentioned disadvantages of the heretofore-known devices and methods of this general type, which are comfortable to use, inexpensive and disposable.

The invention of the instant application has many advantages over prior art devices, which include: a) the invention is undetectable when worn, b) the invention is comfortable to wear, c) the invention is inexpensive to manufacture, d) the invention is disposable, and e) the invention is reliable.

A unique feature of the invention of the instant application is that each safe sex assurance device is given a unique serial number. The safe sex assurance device can only be removed by destroying the device, therefore, the same safe sex assurance device can never be used twice. As each safe sex assurance device has a unique serial number, the replacement of the original device will be clearly shown by the different serial number.

With the foregoing and other objects in view there is provided, in accordance with the invention, a device, comprising a plurality of loop members; a plurality of longitudinal members interconnecting the plurality of loop members; and a testicle retaining ring for receiving and securing to testicles, the testicle receiving ring has a locking member disposed thereon and is attached to one of the longitudinal members, the locking member adjusts and maintains a selected circumference of the retaining ring for receiving and securing the testicles.

In accordance with an added feature of the invention, at least one of the longitudinal members has a plurality of barb members.

In accordance with another feature of the invention, the loop members, the longitudinal retaining members and the retaining ring are made from nylon.

In accordance with an additional feature of the invention, there is a strap which has two ends and is connected on one end to the testicle retaining ring and on the other of the ends to one of the longitudinal members.

In accordance with yet another added feature of the invention, the strap has a label displaying a unique identification.

In accordance with yet another additional feature of the invention, the unique identification is a serial number.

In accordance with a concomitant feature of the invention, each of the loop members has an locking member disposed thereon to adjust and maintain a selected circumference of each of the loop members.

With the foregoing and other objects in view there is further provided, in accordance with the invention, a second device comprising a back member; a frontal netting having a pair of side strings, the side strings are connected to the back member; a label displaying a unique identification associated with the netting; an upper string connected to the back member; a pair of bottom strings having a first end and a second end, the first end is connected to the netting member and the second end is connected to the back member; and the upper string and the side strings each having a locking member to adjust and maintain a length of the upper string and the side strings.

In accordance with an added feature of the invention, the unique identification is a serial number.

Other characteristic features of the invention are set forth in the appended claims.

Although the invention is illustrated and described herein as embodied in safe sex assurance devices, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of specific embodiments when read in connection with the accompanying drawings.

DESCRIPTION OF THE PREFERRED EMBODIMENTS

Figure 1:
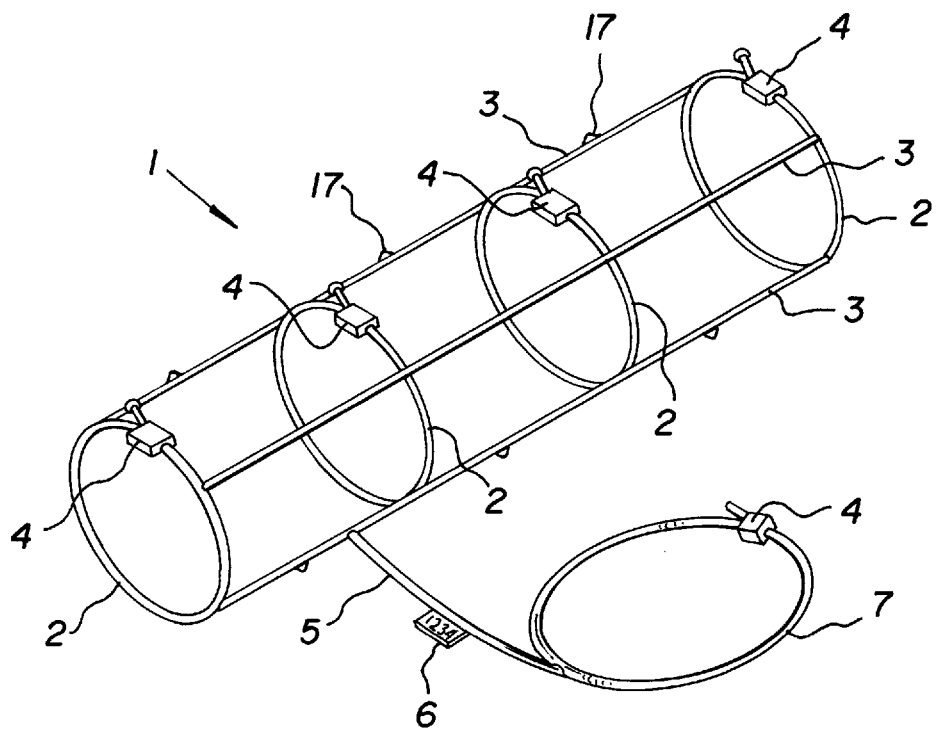
FIG. 1 is a diagrammatic, perspective view of a male safe sex assurance device.

Referring now to the figures of the drawings in detail and first, particularly, to FIG. 1 thereof, there is shown a safe sex assurance device 1 configured for the male gender. The male safe sex assurance device 1 has a plurality of loop members 2 interconnected by a plurality of longitudinal support members 3. Associated with each loop member 2 is a locking member 4 for securing the loop member 2. Connected to one of the longitudinal members 3 is a strap 5. The strap 5 has a label 6 which carries an identification or serial number. The male safe sex assurance device 1 also has a testicle retaining ring 7 connected to the strap 5. The testicle retaining ring 7 also has the locking member 4 for adjusting a circumference of the testicle retaining ring 7.

Figure 2A:
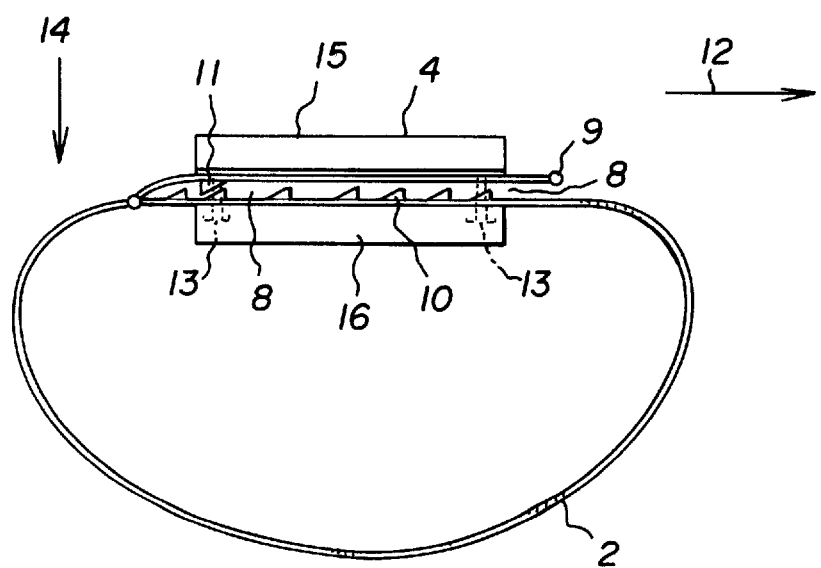
FIGS. 2a and 2b are enlarged, side-elevational views of a locking member in an open and a closed position.
Figure 2B:
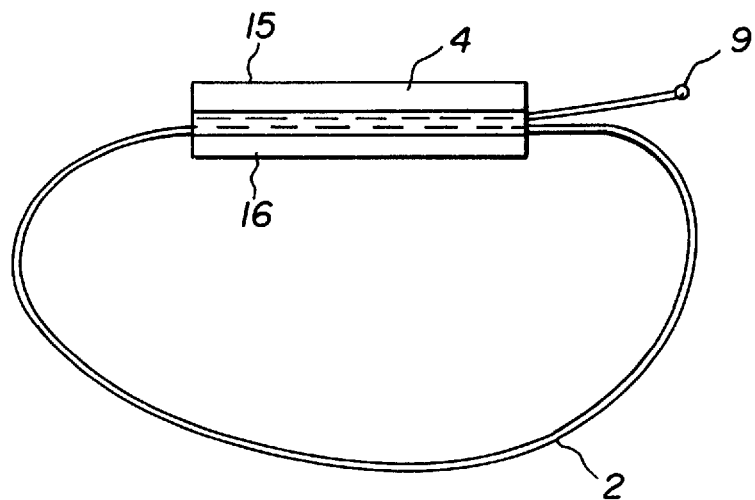

FIGS. 2a and 2b show enlarged views of the locking member 4 and the loop member 2. The loop member 2 is made of a thin, netting material. The netting material being made from either a fabric such as nylon or a plastic. The locking member 4 is shown in the open position in FIG. 2a. The opened locking member 4 has a channel 8 for receiving the loop member 2. The loop member 2 has a pull member 9 with a locking tooth 11. The loop member 2 also has a plurality of engaging teeth 10. The pull member 9 of the loop member 2 is pulled in the direction of arrow 12 in order to reduce the circumference of the loop member 2. Once set, the circumference of the loop member 2 is maintained by the interlocking nature of the locking tooth 11 on the pull member 9 with one of the engaging teeth 10. The locking member 4 also has a set of locking feet 13. After the circumference of the locking member 4 has been achieved, a top portion 15 of the locking member 4 is pushed down in the direction of arrow 14. The locking feet 13 are engaged by the walls of a lower member 16 of the locking member 4 and the locking member 4 is now in the closed position as shown in FIG. 2b. Once locked, the locking mechanism cannot be reopened because the locking feet 13 cannot be disengaged from the lower member 16 without breaking off the locking feet 13. Of course, other locking mechanisms can be used such as those used in plastic handcuffs. The object of the locking mechanism is that once engaged, the locking mechanism cannot be released.

In use, the loop members 2 of the male safe sex assurance device 1 are placed over the male sex organ. The locking members 4 are then individually tightened around the sex organ and once the adjustment is achieved, the locking mechanism is closed. The testicle retaining ring 7 is then secured and tightened around the testicles. The male safe sex assurance device 1 can only be removed by cutting away the male safe sex assurance device 1 with scissors or a similar cutting device. Once removed, the male safe sex assurance device cannot be reused. Each male safe sex assurance device 1 has its own unique serial number. Should one remove the male safe sex assurance device 1, one cannot reuse the same male safe sex assurance device 1. A newly attached male safe sex assurance device 1 would carry a different serial number. Therefore, it would be obvious to ones sexual partner if one has detached the original male safe sex assurance device 1 and replaced it with another.

Optionally, the longitudinal members 3 can have a plurality of barbed members 17 disposed along the length of the of the longitudinal members 3 (see FIG. 1). The barbed members 17 provide an uncomfortable environment should the user attempt to have intercourse while wearing the male safe sex assurance device 1.

As can be derived from the invention, it is inexpensive to manufacture, disposable, compact in size and easily hidden when wearing cloths.

Figure 4:
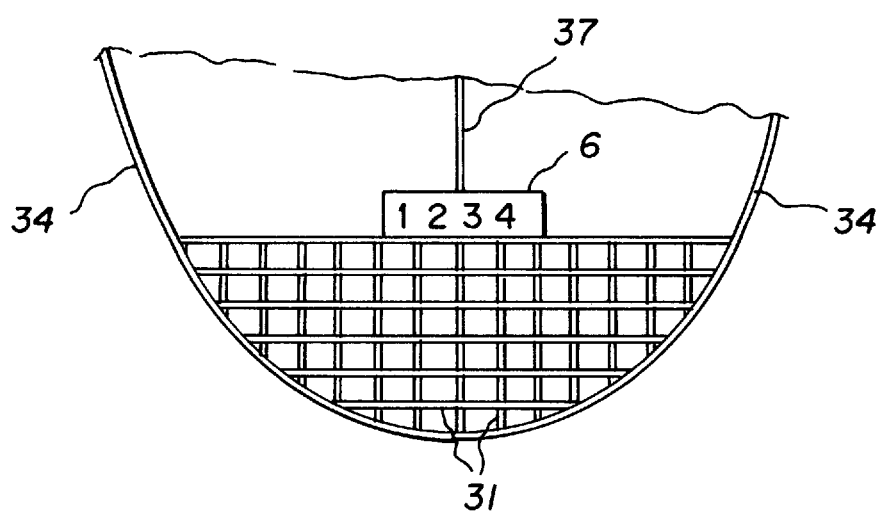
FIG. 4 is a fragmentary, front elevational view of the female safe sex assurance device.
Figure 3:
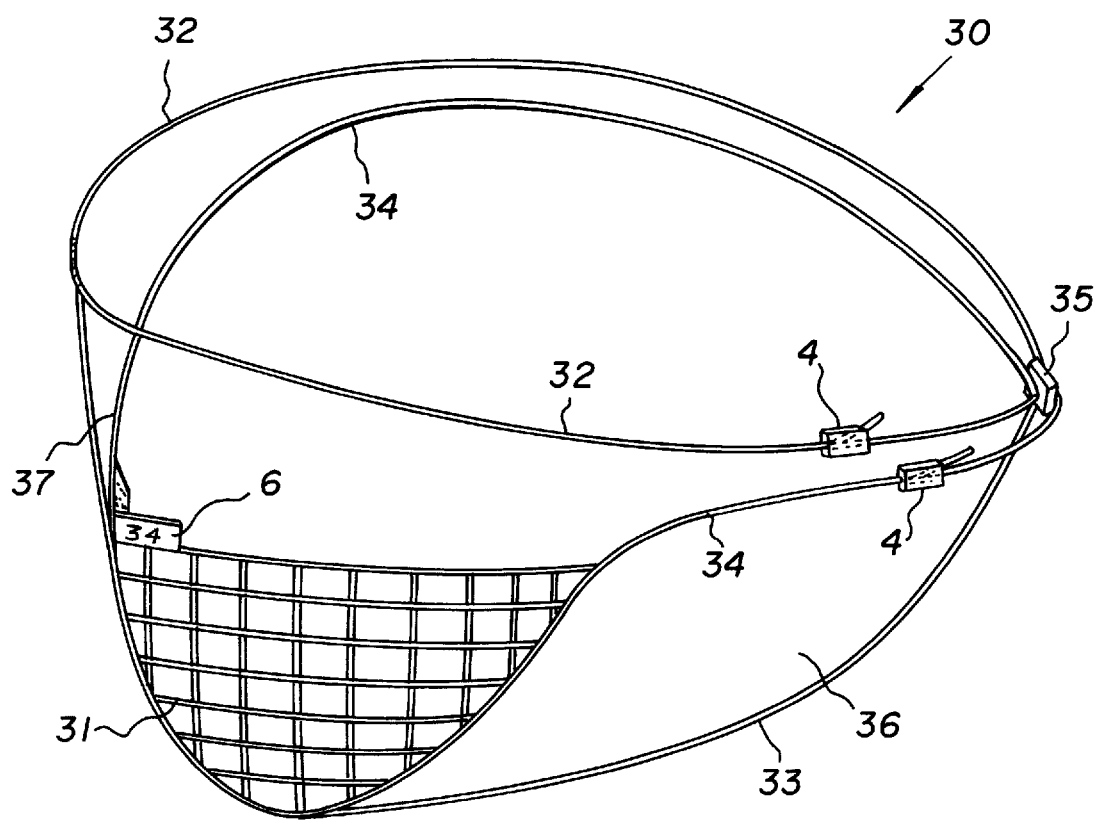
FIG. 3 is a side-elevational view of a female safe sex assurance device.

FIG. 3 shows a female safe sex assurance device 30. The female safe sex assurance device 30 is composed of a frontal netting member 31. Above the frontal netting member 31 is the label 6 displaying a serial number. FIG. 4 shows a better view of the label 6. The frontal netting 31 has a pair of side strings 34 which are connected to a back member 35. The female safe sex assurance device 30 also has an upper string 32 that forms the upper surface of the female safe sex assurance device 30. A pair of lower stings 33 are connected on one end to the frontal netting 31 and on the other end to the back member 35. A front support string 37 interconnects the upper string 32 with the label 6.

The side strings 34 and the upper string 32 each have a locking member 4 for tightening the female safe sex assurance device 30 to the configuration of the users body. As can be seen from FIG. 3, the female safe sex assurance device 30 is shaped like an undergarment. The safe sex assurance device has two openings or cavities 36 in which the users legs are slipped through. The safe sex assurance device 30 is then fitted to the waist and hips of the user by tightening the upper string 32 and the side strings 34.

As with the male safe sex assurance device 1, the female safe sex assurance 30 is made of a fabric such as nylon or from a plastic material. The female safe sex assurance device 30 can only be removed by cutting the sting members and then removing the female safe sex assurance device 30. Once cut, the female safe sex assurance device 30 cannot be reused.

I claim:

1. A device, comprising:

a plurality of loop members;

a plurality of longitudinal members interconnecting said plurality of loop members; and a testicle retaining ring for receiving and securing to testicles, said testicle receiving ring having a locking member disposed thereon and being attached to one of said longitudinal members, said locking member adjusting and maintaining a selected circumference of said retaining ring for receiving and securing the testicles.

2. The device according to claim 1, wherein at least one of said longitudinal members has a plurality of barb members.

3. The device according to claim 1, wherein said loop members, said longitudinal retaining members and said retaining ring are made from nylon.

4. The device according to claim 1, including a strap having two ends and being connected on one end to said testicle retaining ring and on the other of said ends to one of said longitudinal members.

5. The device according to claim 4, wherein said strap has a label displaying a unique identification.

6. The device according to claim 5, wherein said unique identification is a serial number.

7. The device according to claim 1, wherein each of said loop members has an locking member disposed thereon for adjusting and maintaining a selected circumference of each of said loop members.

* * * * *